United States Patent [19]

Morita et al.

[11] Patent Number: 5,041,644

[45] Date of Patent: Aug. 20, 1991

[54] PEPTIDE DERIVATIVES OF β-CHLORO-L(Z)-DEHYDRO-GLUTAMIC ACID

[75] Inventors: Yoshiharu Morita; Ryoichi Ando; Junko Takashima, all of Yokohama, Japan; Louis Chaiet, Springfield, N.J.

[73] Assignee: Merck & Co., Inc., Rahway, N.J.

[21] Appl. No.: 211,618

[22] Filed: Jun. 27, 1988

[30] Foreign Application Priority Data

Jul. 6, 1987 [JP] Japan ............................. 62-160355

[51] Int. Cl.$^5$ ................. C07C 229/20; C07C 229/38; C07D 233/64; C07K 5/00
[52] U.S. Cl. .................................. 562/565; 562/426; 562/440; 562/445; 562/448; 562/449; 562/556; 562/560; 562/561; 562/564; 548/344; 548/531; 548/557; 548/495; 530/328; 530/329; 530/330; 530/331
[58] Field of Search ...................... 548/344, 496, 557; 562/426, 440, 445, 448, 449, 556, 560, 561, 564, 565; 530/330, 331, 328, 329

[56] References Cited

U.S. PATENT DOCUMENTS

| | | | |
|---|---|---|---|
| 4,147,780 | 4/1979 | Dingwall | 530/328 |
| 4,160,452 | 7/1979 | Theeuwes | 530/328 |
| 4,256,108 | 3/1981 | Theeuwes | 530/328 |
| 4,265,874 | 5/1981 | Bonsen et al. | 530/328 |
| 4,374,131 | 2/1983 | Petrillo | 530/328 |
| 4,416,833 | 11/1983 | Karanewsky et al. | 530/328 |
| 4,539,208 | 9/1985 | Kahen et al. | 530/328 |
| 4,715,994 | 12/1987 | Parsons et al. | 530/328 |

FOREIGN PATENT DOCUMENTS

| | | |
|---|---|---|
| 0091594 | 10/1983 | European Pat. Off. . |
| 161546 | 11/1985 | European Pat. Off. . |
| 209848 | 1/1987 | European Pat. Off. . |
| 210545 | 2/1987 | European Pat. Off. . |

OTHER PUBLICATIONS

F. Arndt Organic Syn. Coll. V II 165–167 p. 33 (1943).
F. R. Atherton et al., Antimicrobial Agents & Chemoth. 15, 677 (1979).
P. A. Bartlett and W. B. Kezer J. Amer. Chem. Soc. 106 4282–4283 (1979).
E. K. Baylis et al., J. Chem. Soc. Perkin Trans 1 2845–2853 (1984).
M. Bergmann & H. Schleich, Z. Physiol. Chem. Soc 205 pp. 65–75 (1966).
B. J. Campbell et al, Biochem Biophys Acta 118 pp. 371–386 (1966).
Chem Abstracts, vol. 107, No. 11, No. 97134k (1987).
Chem Abstracts, vol. 107 (9) No. 78205d (1987).
Chaiet et al, J. Antibiotics 37 (3) 207–210 (1984).
Gundermann et al, Chem. Ber. 94 3254 (1961).
F. M. Kahan, et al J. Antimicrobial Chemo. 12, Suppl. D. 1–35 (1983).
Lesiak et al Polish J. Chem. 53 327 (1979).
Neuhaus J. Biol. Chem., 778 (1962).
F. C. Neuhaus & W. P. Hammes, Pharm. Ther. 14 265–319 (1981).
F. C. Neuhaus & J. L. Lynch Biochemistry 3 471–480 (1964).
F. C. Neuhaus et al., Biochemistry 8 5119–5124 (1969).
A. Rahman et al. Tetrahedron 36 1063–1070 (1980).
E. D. Thorsett, et al (Merck & Co., Inc. Proc. Natl. Acad. Sci. U.S.A. vol. 79 2176–2180 (Apr. 1982).
J. K. Thottathil et al. Tetrahedron Lett. 25 4737–40, 4741–44 (1984).

Primary Examiner—Johann Richter
Attorney, Agent, or Firm—Frank P. Grassler; Robert J. North; Hesna J. Pfeiffer

[57] ABSTRACT

New peptide derivatives β-chloro-L-(Z)-dehydroglutamic acid are described which display antibacterial activity.

7 Claims, No Drawings

PEPTIDE DERIVATIVES OF β-CHLORO-L(Z)-DEHYDRO-GLUTAMIC ACID

BACKGROUND OF THE INVENTION

1. Field of the Invention

This invention relates to new β-chloro-L-(Z)-dehydroglutamic acid peptide derivatives as antibacterial agents which interfere in bacterial cell wall synthesis.

2. Brief Description of the Art

Many antibacterial agents owe their selective toxicity to the fact that their targets are structures which are only present in the sensitive bacterium. One of these structures is peptidoglycan a cell wall polymer which plays a vital role in protecting bacteria from lysis. A number of agents, e.g., β-lactams, bacitracin, and flavomycin, interfere with the assembly of this polymer by inhibiting enzymatic reactions involved in the final stages of assembly.

Peptidoglycan biosynthesis involves a precursor, UDP-MurNAc-Ala-D-Glu-Lys-D-Ala-D-Alanine that is biosynthesized in a multienzyme pathway which terminates in the addition of D-Alanine-D-Alanine to the UDP-MurNAc-tripeptide. The formation of D-Alanyl-D-Alanine is catalyzed by D-Alanyl-D-Alanine ligase (synthetase). It is known that inhibition of D-Alanyl-D-Alanyl ligase will terminate peptidoglycan biosynthesis resulting in vivo in bacterial cell lysis. Such inhibitors can serve as antibacterials. For example, D-Cycloserine, a D-Alanine mimic, is a reversible inhibitor of the ligase at both the donor and acceptor sites and is the most potent ligase inhibitor described heretofore, and is a potent antibacterial. (F. C. Neuhaus et al., *Biochemistry* 3, 471–480 (1964)).

Dipeptide analogs of D-Alanyl-D-Alanine are also known to be inhibitors of ligase. (F. C. Neuhaus et al., *Biochemistry* 8, 5119–5124 (1965), and F. C. Neuhaus and W. P. Hammes, *Pharmac. Ther.* 14, 265–319 (1981)).

With this background, the search for newer and more effective antibacterial agents which are ligase inhibitors, is a continuing one.

SUMMARY OF THE INVENTION

It has been found that compounds of Structure I, shown below, are inhibitors of bacterial cell wall synthesis, and are useful in the treatment of bacterial infections.

By this invention there is provided:

A peptide derivative of β-chloro-L-(Z)-dehydroglutamic acid represented by the general formula (I)

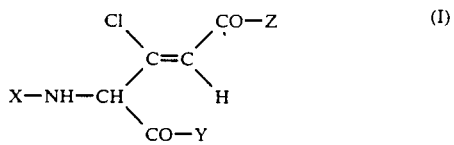

(wherein X is a hydrogen atom or an amino acid or oligopeptide residue obtained by removing, from an amino acid or oligopeptide, the hydroxyl group of the terminal carboxyl group; Y and Z are each a hydroxyl group which may optionally be protected, or an amino acid or oligopeptide residue obtained by removing, from an amino acid or oligopeptide, the hydrogen atom of the terminal amino group; when Y and Z are each said amino acid or oligopeptide residue, each terminal carboxyl group of the respective residues may be protected by a same or different protecting group; and a case is excluded where X is a hydrogen atom and Y and Z are each a hydroxyl group which may optionally be protected).

Also provided is a pharmaceutical composition useful in the treatment of antibacterial infections which comprises a pharmaceutically acceptable carrier and a pharmaceutically effective amount of an antibacterial compound of formula I.

Also provided is a method for treating a bacterial infection in a mammalian host comprising administering to said host a therapeutically effective amount of the above-described composition.

DETAILED EXPLANATION OF THE INVENTION

The present invention relates to peptide derivatives of β-chloro-L-(Z)-dehydroglutamic acid.

β-chloro-L-(Z)-dehydroglutamic acid is a fermentation product of a new strain of *Streptomyces viridogenes*. This substance shows an antibacterial activity but, because of its very narrow antibacterial spectrum, the antibacterial activity is practically limited only to Micrococcus luteus. [L. Chaiet, B. H. Arison, R. L. Monaghan, J. P. Springer, J. L. Smith, S. B. Zimmerman, J. Antibiotics 37 (3) 207 to 210 (1984)].

Excellent bactericides such as β-lactam type semi-synthesized antibiotics have been developed in recent years. However, the emergence of resistant bacteria for these bactericides is inevitable and, as a result, the development of newer bactericides becomes necessary. Accordingly, it is very meaningful to improve the antibacterial effect of β-chloro-L-(Z)-dehydroglutamic acid and thereby to develop a new type of bactericide.

The present inventors have made an extensive research in order to enhance the antibacterial activity of β-chloro-L-(Z)-dehydroglutamic acid and widen its antibacterial spectrum. As a result, it has been found that the remarkable increase of the antibacterial activity of β-chloro-L-(Z)-dehydroglutamic acid as well as the widening of its antibacterial spectrum can be obtained by bonding amino acids or oligopeptides to the terminal amino group, α-position carboxyl group and γ-position carboxyl group of β-chloro-L-(Z)-dehydroglutamic acid to convert it to a peptide derivative. This finding has led to the completion of the present invention.

The peptide derivatives of β-chloro-L-(Z)-dehydroglutamic acid according to the present invention may have protecting groups which can change into substantial active substances in living bodies.

The peptide derivatives of β-chloro-L-(Z)-dehydroglutamic acid can be used for medical treatment as they are. They can also be used for the same purpose in a non-toxic salt form. As such a salt, there can be mentioned, as a salt of amine, mineral acid salts such as hydrochloride, hydrobromide and sulfate, and non-toxic organic acid salts and; as a salt of carboxylic acid, alkali metal salts and alkaline earth metal salts, including sodium salt, potassium salt, calcium salt and magnesium salt, ammonium salts and non-toxic organic amine salts.

In Y and Z of the general formula (I), when Y and Z are each a hydroxyl group which may optionally be protected, the protecting group refers to a protecting group which can be removed in vivo. As such a protecting group, there can be mentioned straight chain or branched chain alkyl groups of 1 to 10 carbon atoms optionally having a substituent, such as methyl, ethyl, propyl, tert-butyl, methoxymethyl, acetoxymethyl, pivaloyloxymethyl, benzyl, p-nitrobenzyl, p-methoxybenzyl and phthalidyl, as well as aryl groups optionally having a substituent, such as phenyl and indanyl. In X, Y and Z, the respective amino acid residues may be same or different and include residues of amino acids such as glycine, alanine, valine, norvaline, leucine, isoleucine, serine, threonine, phenylalanine, tyrosine, tryptophane, histidine, aspartic acid, asparagine, glutamic acid, glutamine, lysine, arginine, cysteine, methionine, proline and the like. Preferably, there can be mentioned residues of amino acids such as glycine, alanine, valine, norvaline, leucine, isoleucine, serine, cystein, methionine and the like. Also, the respective oligopeptide residues may be same or different and are constituted by 2 to 10, preferably 2 to 5 or less of the above mentioned amino acids which may be same or different. In Y and Z, the protecting group for each terminal carboxyl group, optionally protected, of the respective amino acid or oligopeptide residues may include those previously mentioned with respect to the hydroxyl group which may optionally be protected.

Preferably, X may include a hydrogen atom; or a residue of amino acid of L-alanine or L-norvaline, or an oligopeptide residue constituted of 2 of the above mentioned amino acids.

Preferably, Y and X are respectively an OH group optionally having a substituent of $C_1$-$C_5$ alkyl group; or a residue of amino acid of L-alanine or L-norvaline, optionally having a substituent of $C_1$-$C_5$ alkyl group, or an oligopeptide residue constituted of 2 of the above mentioned amino acids.

Preferably, Y is an OH group optionally having a substituent of $C_1$-$C_3$ alkyl group, particularly. And particularly preferable, Z is an OH group; or a residue of amino acid of L-alanine or L-norvaline, optionally having a substituent of $C_1$-$C_3$ alkyl group, or an oligopeptide residue constituted of 2 of the above mentioned amino acids.

In amino acids including those constituting oligopeptides, there exist optical isomers. They can be any of L-, D- and DL-amino acids. L-amino acids are used in most cases.

Hence, the following compounds can be mentioned as specific examples of the peptide derivatives of β-chloro-L-(Z)-dehydroglutamic acid of the present invention.

1. L-alanyl-β-chloro-L-(Z)-dehydroglutamic acid
2. L-norvalyl-β-chloro-L-(Z)-dehydroglutamic acid
3. L-alanyl-L-alanyl-β-chloro-L-(Z)-dehydroglutamic acid
4. Methyl ester of β-chloro-L-(Z)-dehydroglutamyl-L-norvaline
5. Methyl ester of β-chloro-ε-(1-methoxycarbonylbutyl)-L-(Z)-dehydroglutaminyl-L-norvaline The present invention will be described in more detail by explaining typical process for producing the present compounds. However, the present invention is in no way restricted to these processes.

The peptide derivatives of β-chloro-L-(Z)-dehydroglutamic acid of the present invention can ordinarily be produced according to the following process A or B.

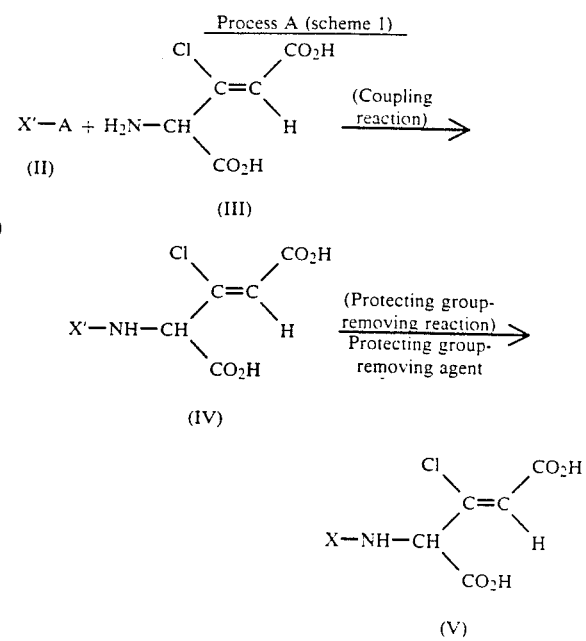

[In the scheme 1, X has the same definition as in the general formula (I) but excludes a case of being a hydrogen atom; X' is same as X with a proviso that the amino group is protected; and A is an activated group for the carboxyl group.]

In this process, β-chloro-L-(Z)-dehydroglutamic acid represented by the general formula (III) and an active derivative of an amino-group-protected amino acid or oligopeptide represented by the general formula (II) are subjected to a coupling reaction in an appropriate solvent to produce an intermediate represented by the general formula (IV); and the intermediate is subjected to a protecting group-removing reaction in the presence of a protecting group-removing agent to obtain a desired product represented by the general formula (V).

The coupling reaction and the protecting group-removing reaction can be conducted by employing reactions ordinarily used in peptide synthetic chemistry. Therefore, as the protecting group for the amino group of X', there can be mentioned, for example, a carbobenzoxy group, a p-methoxybenzyloxycarbonyl group, a tert-butoxycarbonyl group and a trityl group; and the activated group A for the carboxyl group, the solvent and conditions used in the coupling reaction and the conditions used in the protecting group-removing reaction can be selected appropriately, depending upon the purposes, from those ordinarily used in similar reactions. Showing a typical case, β-chloro-L-(Z)-dehydroglutamic acid represented by the general formula (III) and a N-hydroxysuccinimide ester of an amino acid or oligopeptide whose amino group is protected by a tert-butoxycarbonyl group, represented by the general formula (II) are reacted overnight at room temperature in a mixed solvent of ethanol and water in the presence of sodium hydrogencarbonate, whereby an intermediate represented by the general formula (IV) is produced conveniently. This intermediate is subjected to protecting group-removing reaction according to an ordinary method. For example, the intermediate is subjected to protecting group-removing reaction at room temperature using, as protecting group-removing agent, an acetic acid solution saturated with hydrogen bromide, whereby a desired product represented by the general formula (V) can be obtained in a hydrobromide form. If desired, the hydrobromide can further be treated with, for example, propylene oxide according to an ordinary method, whereby hydrogen bromide is removed and an intramolecular salt is obtained.

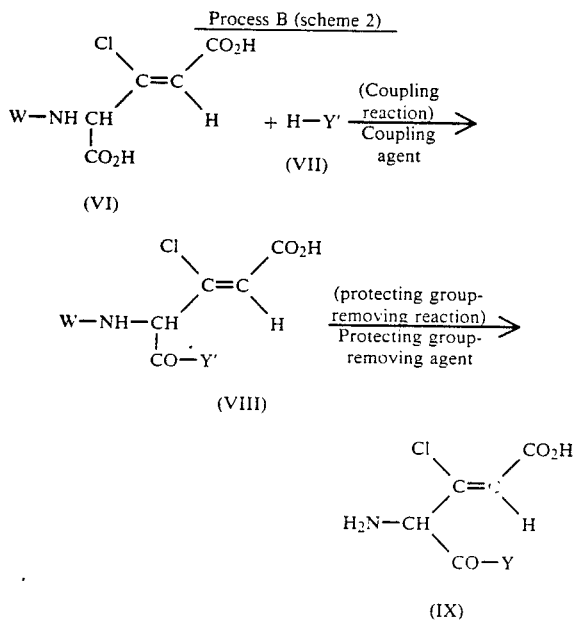

[In the scheme 2, Y has the same definition as in the general formula (I) but excludes a case of being a hydroxyl group optionally having a protecting group; W is a protecting group for the amino group; and Y' is same as the Y of the general formula (I) whose carboxyl group may be protected.]

In this process, β-chloro-L-(Z)-dehydroglutamic acid having a protected amino group, represented by the general formula (VI) and an amino acid or oligopeptide whose carboxyl group may be protected, represented by the general formula (VII) are subjected to a coupling reaction in an appropriate solvent in the presence of a coupling agent to produce an intermedaite represented by the general formula (VIII). Then, the intermediate is subjected to a protecting group-removing reaction in the presence of protecting group-removing agent to obtain a desired product represented by the general formula (IX).

The coupling reaction and the protecting group-removing reaction can be conducted by employing reactions ordinarily used in peptide synthetic chemistry. Accordingly, as the protecting group for the carboxyl group of Y', there can be mentioned, for example, a benzyl group, a p-methoxybenzyl group and a tert-butyl group. The carboxyl group of Y is protected by a protecting group which can be removed in vivo, or a protecting group same as that of the carboxyl group of Y . The coupling agent, solvent and conditions used in the coupling reaction, the conditions used in the protecting group-removing reaction, and the conditions for selectively removing the protecting group W for the amino group in the general formula (VIII) when the carboxyl group of Y has a protecting group which can be removed in vivo, can be selected appropriately depending upon the purpose, from those ordinarily used in similar reactions. Showing a typical case, β-chloro-L-(Z)-dehydroglutamic acid having an amino group protected by a tert-butoxycarbonyl group and an alkyl ester of an amino acid are reacted overnight at 0° C. to room temperature in an mixed solvent of acetonitrile and dioxane using dicyclohexylcarbodiimide as a coupling agent, to produce, as an intermediate, an alkyl ester of N-tert-butoxycarbonyl-β-chloro-L-(Z)-dehydroglutamyl-L-norvaline represented by the general formula (VIII). This intermediate is further subjected to protecting group-removing reaction according to an ordinary method. For example, when the intermediate is subjected to protecting group-removing reaction for 5 minutes at room temperature using, as a protecting group-removing agent, an acetic acid solution saturated with hydrogen bromide, the tert-butoxycarbonyl group-represented by W which is a protecting group for the amino group is removed with the alkyl group (a protecting group for the carboxyl group) being unremoved, whereby a desired product represented by the general formula (IX) is obtained in a hydrobromide form. If desired, the hydrobromide is further treated with propylene oxide according to an ordinary method, whereby hydrogen bromide is removed therefrom and an intramolecular salt is obtained.

By applying the process B (the scheme 2), there can further be produced a peptide derivative of β-chloro-L-(Z)-dehydroglutamic acid represented by the general formula (X)

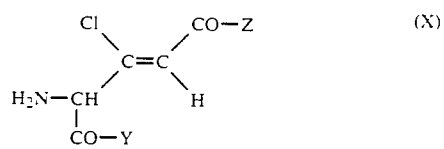

[wherein Y and Z have the same definitions as in the general formula (I), respectively, but exclude a case of being each a hydroxyl group which may optionally be protected].

A peptide derivative of β-chloro-L-(Z)-dehydroglutamic acid represented by the general formula (I)

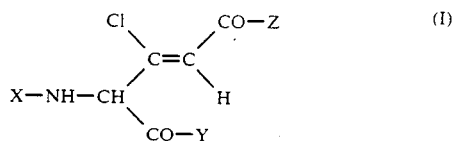

(wherein X, Y and Z have the same definitions as given previously, respectively) can be produced by appropriately combining the process A and the process B, or appropriately adopting reactions ordinarily used in peptide synthetic chemistry and, if necessary, protecting the hydroxyl group of Y or Z before or after the reactions.

The separation and purification of the intermediate and the end product produced according to the above-mentioned process requires no special method and can be conducted easily by using well known methods ordinarily used for such purposes, such as solvent extraction, washing, crystallization, ion exchange resin and column chromatography.

The pharmaceutical composition of the invention useful in the treatment of antibacterial infections preferably comprises a pharmaceutically acceptable carrier and a pharmaceutically effective amount of an antibacterial compound of formulae I.

For administration, the compositions of the invention can also contain other conventional pharmaceutically acceptable compounding ingredients, as necessary or desired. Such ingredients are generally referred to as carriers or diluents. Conventional procedures for preparing such compositions in appropriate dosage forms can be utilized. Whatever the dosage form, it will contain a pharmaceutically effective amount of the compounds of the invention.

The present compositions can be administered parenterally and this is preferred when they are used in combination with a carbapenem antibiotic such as imipenem. They may also be administered orally. The compounds of this invention may also be used to treat topical antibacterial infection. Therefore, these compounds may be presented in a number of appropriate dosage forms; e.g., tablets, capsules, suspensions, solutions, and the like, for oral administration; solutions, suspensions, emulsions, and the like, for parenteral administration; solutions for intravenous administration; and ointments, transdermal patches, and the like, for topical administration.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents which may be (a) a naturally-occurring phosphatide such as lecithin, (b) a condensation product of an alkylene oxide with a fatty acid, for example, polyoxyethylene stearate, (c) a condensation product of ethylene oxide with a long chain aliphatic alcohol, for example, heptadecaethyleneoxycetanol, (d) a condensation product of ethylene oxide with a partial ester derived from a fatty acid and a hexitol such as polyoxyethylene sorbitol monooleate, or (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

For topical use, creams, ointments, jellies, solutions or suspensions, etc., containing the compositions of the invention are employed.

Treatment dosage for human beings can be varied as necessary. Generally, oral dosages of the antibacterial compounds of this invention when given orally are in the range 250 mg to 4 g per patient given 3-4 times daily. The intravenous or intramuscular dosages are 100 mg to 1 g given 3-4 times daily. When the compounds of the invention are given intravenously or intramuscularly to potentiate carbapenem antibiotics such as imipenem they are given in combination with the antibiotic in amounts of 0.1-10 mg/kg/day.

The amount of active ingredient that may be combined with the carrier materials to produce a single dosage form will vary depending upon the host treated and the particular mode of administration. For example, a formulation intended for oral administration may contain, for example, from 100 mg to 2000 mg of active agent compounded with an appropriate and convenient amount of carrier material which may vary from about 5 to about 95 percent of the total composition.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The present invention will be explained in more detail below by way of Reference Example and Examples.

REFERENCE EXAMPLE

N-tert-butoxycarbonyl-$\beta$-chloro-L-(Z)-dehydroglutamic acid 1.12 g (6.24 mM) of $\beta$-chloro-L-(Z)-dehydroglutamic acid was dissolved in water. Thereto was added 1.58 g (15.6 mM) of triethylamine. There was further added 10 ml of a dioxane solution containing 1.65 g (6.86 mM) of tert-butyl 4,6-dimethylpyrimidyl-2-thiolcarbonate. The mixture was stirred overnight at room temperature. After the reaction, 70 ml of water was added to the reaction mixture. The whole mixture was washed with ethyl acetate. To the resulting aqueous layer was added concentrated hydrochloric acid to make the layer acidic. The aqueous layer was then extracted with ethyl acetate. The extract was washed with 2N-hydrochloric acid and a saturated aqueous sodium chloride solution in this order, dried with $MgSO_4$ and subjected to vacuum distillation to remove ethyl acetate. The residue was purified by means of reversed phase column chromatography (developing solvent and elutant: water-methanol) to obtain 1.31 g (yield: 75%) of the captioned compound. NMR ($CD_3OD$) 1.44 [9H,s, $C(CH_3)_3$], 5.00 (1H, s, —CH—) 6.43 (1H, s, C=CH—)

EXAMPLE 1

L-alanyl-$\beta$-chloro-L-(Z)-dehydroglutamic acid (a) 540 mg (3.0 mM) of $\beta$-chloro-L-(Z)-dehydroglutamic acid and 940 mg (3.3 mM) of N-tert-butoxycarbonyl-L-alanine hydroxysuccinimide ester were dissolved in a mixture of 25 ml of ethanol and 30 ml of 0.3M aqueous solution containing sodium hydrogencarbonate. The solution was stirred overnight at room temperature. After the reaction, the solvent was removed by vacuum distillation. The residue was dissolved in water. The solution was washed with ethyl acetate. To the aqueous layer was added concentrated hydrochloric acid to make the layer acidic. The resulting layer was extracted with ethyl acetate. The extract was washed with a saturated aqueous sodium chloride solution, dried with $MgSO_4$ and subjected to vacuum distillation to remove ethyl acetate. The residue was purified by means of reversed phase column chromatograph ($C_8$) (developing and eluting solvent: water-methanol) to obtain 860 mg (yield: 81%) of N-tert-butoxycarbonyl L-alanyl-$\beta$-chloro-L-(Z)-dehydroglutamic acid.

IR (neat, cm$^{-1}$) 1740-1640, 1520

NMR ($\delta$, $CD_3OD$) 1.32 (3H, d, J=7 Hz, —$CH_3$), 1.43 [9H, s, $C(CH_3)_3$], 4.15 (1H, q, J=7 Hz, —CH—), 5.25 (1H, s, —CH—), 6.45 (1H, s, C=CH—)

(b) 770 mg (2.17 mM) of N-tert-butoxycarbonyl-L-alanyl-$\beta$-chloro-L-(Z)-dehydroglutamic acid was dissolved in 10 ml of an acetic acid solution saturated with hydrogen bromide. The solution was stirred for 15 minutes at room temperature. Diethyl ether was added to the reaction mixture. The resulting crystal was collected by filtration and washed with diethyl ether. The crystal (hydrobromide salt) obtained was dissolved in 20 ml of ethanol. Thereto was added 5 ml of propylene oxide, and the mixture was allowed to stand for a while. The resulting crystal was collected by filtration and washed with ethanol and ether in this order. The crystal thus obtained was purified using reversed phase column chromatograph ($C_8$) (developing and eluting solvent: water) to obtain 270 mg (yield: 50%) of the captioned compound.

Melting point=147° to 149° C. (decomposed)

IR (KBr, cm$^{-1}$ 1680, 1640, 1545

NMR ($D_2O$) 1.58 (3H, d, J=7 Hz, —$CH_3$), 4.18 (1H, q, J=7 Hz, —CH—), 4.96 (1H, s, —CH—), 6.43 (1H, s, CH=C)

EXAMPLE 2

L-norvalyl-$\beta$-chloro-L-(Z)-dehydroglutamic acid (a) 359 mg (2.0 mM) of $\beta$-chloro-L-(Z)-dehydroglutamic acid and 628 mg (2.0M) of N-tert-butoxycarbonyl-L-norvaline N-hydroxysuccinimide ester were dissolved in a mixture of 5 ml of ethanol and 50 ml of 1.2M aqueous solution of sodium hydroxide. The solution was stirred overnight at room temperature. After the reaction, the solvent was removed by vacuum distillation. The residue was dissolved in water. The resulting solution was washed with ether. Citric acid was added to the aqueous layer to make it acidic and the aqueous layer was then extracted with ethyl acetate. The extract was washed with a saturated aqueous sodium chloride solution, dried with $Na_2SO_4$ and subjected to vacuum distillation to remove ethyl acetate. The residue was purified by means of reversed phase silica gel column chromatography ($C_{18}$) (developing and eluting solvent: water-methanol) to obtain 620 mg (yield: 82%) of N-tert-butoxycarbonyl-L-norvalyl-$\beta$-chloro-L-(Z)-dehydroglutamic acid as an oily substance.

NMR ($\delta$, $CD_3OD$) 0.90 (3H, t, $CH_2CH_3$), 1.45 [9H, s, $C(CH_3)_3$], 1.2-2.0 (4H, m, —$CH_2CH_2$—), 3.9-4.3 [1H, m, N—CH— (norvaline)], 5.30 (1H, s, —CH—C=C), 6.45 (1H, s, C=CH—)

(b) 620 mg (1.64 mM) of N-tert-butoxycarbonyl-L-norvalyl-β-chloro-L-(Z)-dehydroglutamic acid was dissolved in 5 ml of an acetic acid solution saturated with hydrogen bromide. The solution was stirred by shaking for 1 minute at room temperature. Diethyl ether was added to the reaction mixture. The resulting crystal was collected by filtration and washed with diethyl ether. The crystal (hydrobromide) obtained was dissolved in 20 ml of ethanol. To the solution was added 5 ml of propylene oxide, and the mixture was allowed to stand for a while. The resulting crystal was collected by filtration and washed with ethanol to obtain 300 mg (yield: 66%) of the captioned compound.

Melting point = 130° to 132° C. (decomposed)
IR (KBr, cm$^{-1}$) 1715, 1680, 1640, 1605, 1560.
NMR (δ, NaOD+D$_2$O) 0.95 (3H, t, J=7.0 Hz, CH$_2$CH$_3$), 1.2–1.7 (2H, m, CH$_2$CH$_2$CH$_3$), 1.7–2.1 (2H, m, —CH$_2$CH$_2$CH$_3$) 4.10 [1H, t, J=6.5 Hz, N—CH—(-norvaline)], 4.95 (1H, s, —CH—C=C) 6.45 (1H, s, C=CH—)

EXAMPLE 3

L-alanyl-L-alanyl-β-chloro-L-(Z)-dehydroglutamic acid (a) The procedure of Example 1(a) was repeated using 1.04 g (2.91 mM) of tert-butoxycarbonyl-L-alanyl-L-alanine hydroxysuccinimide ester, 360 mg (2.0 mM) of β-chloro-L-(Z)-dehydroglutamic acid, 25 ml of ethanol and 25 ml of 0.24M aqueous solution of sodium hydrogencarbonate to obtain 610 mg (yield: 72%) of N-tert-butoxycarbonyl-L-alanyl-L-alanyl-β-chloro-L-(Z)-dehydroglutamic acid.

IR (KBr, cm$^{-1}$) 1720–1640, 1525
NMR (δ, CD$_3$OD) 1.27–1.45 (m, 6H, —CH$_3$), 1.43 (9H, s, —C(CH$_3$)$_3$), 4.07 (1H, q, J=7 Hz, —CH—), 4.47 (1H, q, J=7 Hz, —CH—), 5.17 (1H, s, —CH—), 6.45 (1H, s, C=CH—)

(b) The procedure of Example 2(b) was repeated using 610 mg (1.45 mM) of N-tert-butoxycarbonyl-L-alanyl-L-alanyl-β-chloro-L-(Z)-dehydroglutamic acid, 7 ml of an acetic acid solution saturated with hydrogen bromide, 20 ml of ethanol and 5 ml of propylene oxide and stirring by shaking for 5 minutes in place of 1 minute, whereby 330 mg (yield: 80%) of the captioned compound was obtained.

Melting point = 146° to 148° C. (decomposed)
IR (KBr, cm$^{-1}$) 1655, 1640, 1540
NMR (δ, D$_2$O) 1.43 (3H, d, J=7 Hz, —CH$_3$), 1.57 (3 H, d, J=7 Hz, —CH$_3$). 4.15 (1H, q, J=7 Hz, —CH—), 4.48 (1H, q, J=7 Hz, —CH—), 4.94 (1H, s, —CH—), 6.45 (1H, s, C=CH—)

EXAMPLE 4

Methyl ester of β-chloro-ε-(1-methoxycarbonylbutyl)-N-tert-butoxycarbonyl-L-(Z)-dehydroglutaminyl-L-norvaline and methyl ester of N-tert-butoxycarbonyl-β-chloro-L-(Z)-dehydroglutamyl-L-norvaline A mixture of 530 mg (4.05 mM) of methyl ester of L-norvaline, 50 ml of acetonitrile, 10 ml of dioxane and 1.13 g (4.05 mM) of N-tert-butoxycarbonyl-β-chloro-L-(Z)-dehydroglutamic acid was cooled to 0° C. Thereto was added 830 mg (4.05 mM) of dicyclohexylcarbodiimide. The mixture was stirred overnight at 0° C. to room temperature. After the reaction, the solvent was removed by vacuum distillation. The residue was dissolved in an aqueous sodium hydrogencarbonate solution. The solution was extracted with ethyl acetate. The extract was washed with a saturated aqueous sodium chloride solution, dried with MgSO$_4$ and then subjected to vacuum distillation to remove the ethyl acetate, whereby a crude product A was obtained. Meanwhile, concentrated hydrochloric acid was added to the aqueous layer to make the layer acidic. The resulting layer was extracted with ethyl acetate. The extract was washed with a saturated aqueous sodium chloride solution, dried with MgSO$_4$ and then subjected to vacuum distillation to remove ethyl acetate, whereby a crude product B was obtained.

The crude product A was purified by means of silica gel column chromatography (developing and eluting solvent: hexane-ethyl acetate) to obtain 136 mg (yield: 6.6%) of methyl ester of β-chloro-ε-(1-methoxycarbonylbutyl)-N-tert-butoxycarbonyl-L-(Z)-dehydroglutaminyl-L-norvaline.

NMR (δ, CDCl$_3$), 0.92 (6H, t, J=6 Hz, —CH$_3$), 1.13–2.05 (8H, —CH$_2$CH$_2$—), 1.45 (9H, s, C(CH$_3$)$_3$), 3.72 (6H, s, OCH$_3$) 4.32–4.83 (2H, m, —CH—), 5.02 (1H, d, J=7 Hz, —CH—), 5.87 (1H, d, J=7 Hz, CONH), 6.48 (1H, s, C=CH—), 6.90 (1H, d, J=8 Hz, CONH), 7.07 (1H, d, J=8 Hz, CONH)

The crude product B was purified by means of reversed phase column chromatography (C$_8$) (developing and eluting solvent: water-methanol) to obtain 380 mg (yield: 24%) of methyl ester of N-tert-butoxycarbonyl-β-chloro-L-(Z)-dehydroglutamyl-L-norvaline.

NMR (δ, CD$_3$OD) 0.70–2.03 (7H, m, —CH$_2$CH$_2$CH$_3$). 1.46 (9H, s, C(CH$_3$)$_3$), 3.70 (3H, s, OCH$_3$), 4.40 (1H, t, J=7 Hz, —CH—), 4.97 (1H, s, —CH—), 6.42 (1H, s, C=CH—)

EXAMPLE 5

Methyl ester of β-chloro-L-(Z)-dehydroglutamyl-L-norvaline 290 mg (0.74 mM) of methyl ester of N-tert-butoxycarbonyl-β-chloro-L-(Z)-dehydroglutamyl-L-norvaline was dissolved in an acetic acid solution saturated with hydrogen bromide. The solution was stirred for 5 minutes at room temperature. Diethyl ether was added to the reaction mixture. The resulting crystal was collected by filtration and washed with diethyl ether The crystal (hydrobromide) thus obtained was dissolved in 20 ml of ethanol. To the solution was added 5 ml of propylene oxide, and the mixture was allowed to stand for a while and then 10 ml of diethyl ether was added. The resulting crystal was collected by filtration and washed with diethyl ether to obtain 170 mg (yield: 79%) of the captioned compound.

Melting point = 126° to 128.5° C.
IR (KBr, cm$^{-1}$) 1753, 1695, 1595
NMR (δ, D$_2$O+D$_2$SO$_4$) 0.90 (3H, t, J=6 Hz, —CH$_3$), 1.06–2.10 (4H, m, —CH$_2$CH$_2$—), 3.73 (3H, s, OCH$_3$), 4.42 (1H, q, J=7 Hz, —CH—), 5.13 (1H, s, —CH—), 6.83 (1H, s, —CH=C)

EXAMPLE 6

Methyl ester of β-chloro-ε-(1-methoxycarbonylbutyl)-L-(Z)-dehydroglutaminyl-L-norvaline 136 mg (0N27 mM) of methyl ester of β-chloro-ε-(1-methoxycarbonylbutyl)-N-tert-butoxycarbonyl-L-(Z)- dehydroglutaminyl-L-norvaline was dissolved in 1.5 ml of an acetic acid solution saturated with hydrogen bromide. The solution was stirred for 5 minutes at room temperature. 50 ml of ether was added to the reaction mixture. The whole mixture was extracted with a saturated aqueous sodium chloride solution. Sodium hydrogen-carbonate was added to the extract to make the extract basic. The extract was then extracted with ethyl acetate. The resulting extract was washed with a saturated sodium chloride solution, dried with $MgSO_4$ and subjected to vacuum distillation to remove the solvent. The residue was purified by means of silica gel column chromatography (developing and eluting solvent: ethyl acetate) to obtain 66 mg (yield: 61%) of the captioned compound.

IR (neat, $cm^{-1}$) 1740, 1660, 1525

NMR ($\delta$, $CDCl_3$) 0.92 (6H, t, J=6 Hz, $-CH_3$), 1.15-2.05 (8H, m, $-CH_2CH_2-$), 2.13 (2H, s, $-NH_2$), 3.72 (6H, s, $OCH_3$), 4.16 (1H, s, $-CH-$), 4.31-4.85 (2H, m, $-CH-$), 6.33 (1H, s, C=CH-), 7.05 (1H, d, J=7 Hz, CONH), 7.68 (1H, d, J=8 Hz, CONH)

What is claimed is:

1. A compound represented by the general formula (I)

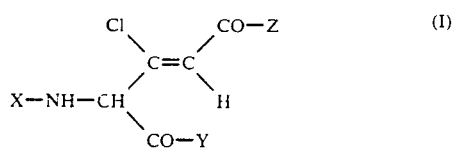

wherein X is a hydrogen atom or an amino acid or oligopeptide residue obtained by removing, from an amino acid or oligopeptide, the hydroxyl group of the terminal carboxyl group; Y and Z are each a hydroxyl group which may optionally be protected, or an amino acid or oligopeptide residue obtained by removing, from an amino acid or oligopeptide, the hydrogen atom of the terminal amino group; when Y and Z are each said amino acid or oligopeptide residue, each terminal carboxyl group of the respective residues may be protected by a same or different protecting group; and a case is excluded where X is a hydrogen atom and Y and Z are each a hydroxyl group which may be protected.

2. A compound according to claim 1, wherein X is a hydrogen atom; a residue of amino acid of glycine, alanine, valine, norvaline, leucine, isoleucine, serine, threonine, phenylalanine, tyrosine, tryptophan, histidine, aspartic acid, asparagine, glutamic acid, glutamine, lysine, arginine, cysteine or methionine, or an oligopeptide residue constituted of 2 to 10 of the above mentioned amino acids, and Y and Z are respectively an OH group optionally having a protecting group of $C_1-C_{10}$ straight chain or branched chain alkyl group optionally having a substituent, or aryl group optionally having a substituent; a residue of amino acid of glycine, alanine, valine, norvaline, leucine, isoleucine, serine, threonine, phenylalanine, tyrosine, tryptophan, histidine, aspartic acid, asparagine, glutamic acid, glutamine, lysine, arginine, cysteine, methionine or proline, optionally having a protecting group selected from $C_1-C_{10}$ straight chain or branched chain alkyl group optionally having a substituent and aryl group optionally having a substituent, or an oligopeptide residue constituted of 2 to 10 of the above mentioned amino acids.

3. A compound according to claim 1, wherein X is hydrogen atom; a residue of amino acid of glycine, alanine, valine, norvaline, leucine, isoleucine, serine, cysteine or methionine, or an oligopeptide residue constituted of 2 to 5 of the above mentioned amino acids, and Y and Z are respectively an OH group optionally having a protecting group selected from $C_1-C_{10}$ alkyl group, methoxymethyl, acetoxymethyl, pivaloyloxymethyl, benzyl, p-nitrobenzyl, p-methoxybenzyl, phthalidyl, phenyl and indanyl; a residue of amino acid of glycine, alanine, valine, norvaline, leucine, isoleucine, serine, cysteine or methionine, optionally having a protecting group selected from $C_1-C_{10}$ alkyl group, methoxymethyl, acetoxymethyl, pivaloyloxymethyl, benzyl, p-nitrobenzyl, p-methoxybenzyl, phthalidyl, phenyl and indanyl, or an oligopeptide residue constituted of 2 to 5 of the above mentioned amino acids.

4. A compound according to claim 1, wherein X is a hydrogen atom; a residue of amino acid of glycine, alanine, valine, norvaline, leucine, isoleucine, serine, cysteine or methionine, or an oligopeptide residue constituted of 2 to 5 of the above mentioned amino acids, and Y and Z are respectively an OH group optionally having a protecting group selected from methyl, ethyl, propyl, tert-butyl, methoxymethyl, acetoxymethyl, pivaloyloxymethyl, benzyl, p-nitrobenzyl, p-methoxybenzyl, phthalidyl, phenyl and indanyl; a residue of amino acid of glycine, alanine, valine, norvaline, leucine, isoleucine, serine, cysteine or methionine, optionally having a protecting group selected from methyl, ethyl, propyl, tert-butyl, methoxymethyl, acetoxymethyl, pivaloyloxymethyl, benzyl, p-nitrobenzyl, p-methoxybenzyl, phthalidyl, phenyl and indanyl, or an oligopeptide residue constituted of 2 to 5 of the above mentioned amino acids.

5. A compound according to claim 1 wherein X is a hydrogen atom; a residue of amino acid of L-alanine or L-norvaline, or an oligopeptide residue constituted of 2 of the above mentioned amino acids, and Y and Z are respectively an OH group optionally having a substituent of $C_1-C_5$ alkyl group; a residue of amino acid of L-alanine or L-norvaline, optionally having a substituent of $C_1-C_5$ alkyl group, or an oligopeptide residue constituted of 2 of the above mentioned amino acids.

6. A compound according to claim 1, wherein X is a hydrogen atom; a residue of amino acid of L-alanine or L-norvaline, or an oligopeptide residue constituted of 2 of the above mentioned amino acids, Y is an OH group optionally having a substituent of $C_1-C_3$ alkyl group, and Z is an OH group; a residue of amino acid of L-alanine or L-norvaline, optionally having a substituent of $C_1-C_3$ alkyl group, or an oligopeptide residue constituted of 2 of the above mentioned amino acids.

7. The compound according to claim 1 selected from:
L-alanyl-$\beta$-chloro-L-(Z)-dehydroglutamic acid;
L-norvalyl-$\beta$-chloro-L-(Z)-dehydroglutamic acid;
L-alanyl-L-alanyl-$\beta$-chloro-L-(Z)-dehydroglutamic acid;
methyl ester of $\beta$-chloro-L-(Z)-dehydroglutamyl-L-norvaline; and
methyl ester of $\beta$-chloro-$\epsilon$-(1-methoxycarbonylbutyl)-L-(Z)-dehydroglutaminyl-L-norvaline.

* * * * *